_United States Patent_ [19]

Tanaka et al.

[11] Patent Number: 4,916,146
[45] Date of Patent: Apr. 10, 1990

[54] AMINO ACID IMIDE DERIVATIVES, USAGE THEREOF, AND MEDICINAL COMPOSITION CONTAINING THE SAME

[75] Inventors: Yoshiaki Tanaka; Tomoji Aotsuka; Naomi Kobayashi; Naoki Nakata; Kuniyoshi Ogura; Motoki Torizuka; Naoyoshi Miura; Heihachiro Arai, all of Konan, Japan

[73] Assignee: Zeria Pharmaceutical Co., Ltd., Tokyo, Japan

[21] Appl. No.: 288,556

[22] Filed: Dec. 22, 1988

[30] Foreign Application Priority Data

Dec. 23, 1987 [JP] Japan .................... 62-326549
Oct. 14, 1988 [JP] Japan .................... 63-256940

[51] Int. Cl.$^4$ ................ C07D 417/02; A61K 31/425
[52] U.S. Cl. .................... 574/365; 548/200; 548/201
[58] Field of Search .................... 548/200; 514/365

[56] References Cited

FOREIGN PATENT DOCUMENTS 036713 9/1981 European Pat. Off. .
173441 3/1986 European Pat. Off. .
232849 8/1987 European Pat. Off. .
280956 9/1988 European Pat. Off. ............ 548/200

OTHER PUBLICATIONS

Beilsteins Handbuch der Organischen Chemie, 4th Edition, vol. 27, part 6, pp. 3954–3955, 1984: Springer-Verlag, Berlin, D; p. 3954, formula VII; p. 3955, lines b–g.
Journal of Biochemistry, vol. 104, No. 4, 1988, pp. 580–586, Nagasaki, J. P.; D. Tsuru et al, "Thiazolidine Derivatives as Potent Inhibitors Specific for Prolyl Endopeptidase".

Primary Examiner—Robert Gerstl
Attorney, Agent, or Firm—Oblon, Spivak, McClelland, Maier & Neustadt

[57] ABSTRACT

Novel N-substituted amino acid imide derivatives are disclosed. The compounds are represented by formula (I):

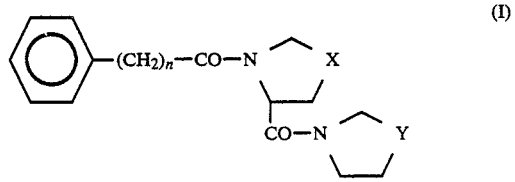

wherein n represents an integer of 0 to 5, and X and Y, which may be the same or different, represent a methylene group or a sulfur atom, provided that not both X and Y are methylene groups at the same time. The compounds are useful as a medicine for treating or preventing cerebral circulation disorder, cerebral metabolism disorder, or memory disturbance.

5 Claims, No Drawings

AMINO ACID IMIDE DERIVATIVES, USAGE THEREOF, AND MEDICINAL COMPOSITION CONTAINING THE SAME

BACKGROUND OF THE INVENTION

1. Field of the Invention

This invention relates to amino acid imide derivatives, and, more particularly, to amino acid imide derivatives possessing prolyl endopeptidase inhibitory activity, antihypoxic activity, and anti-amnesia activity, and hence are useful as a medicine for treating or preventing cerebral circulation disorder, cerebral metabolism disorder, and memory disturbance.

2. Description of the Background

Senile dementia caused by such cerebral disorders as cerebrovascular disorder, cerebral circulation disorder, cerebral metabolism disorder, and memory disturbance has become a social problem in the society with prolonged life-span. Development of medicines useful for treating or preventing these diseases are thus desired.

A recent clinical report [. F. Mazurek et al., Neurology, 36, 1133 (1986)] revealed a remarkable decrease of peptides participating in memory or neurotransmission in brains of senile dementia patients.

Prolyl endopeptidase inhibitors are known as exhibiting anti-amnesic activity, since prolyl endopeptidase hydrolyzes and inactivates neuropeptides including proline(s) in brains such as vasopressin [European Patent Publication No. 232849, Folia Pharmacologica Japonica, 89, 323 (1987), and id., 89, 243 (1987)]. It is also a clinical knowledge that a decreased oxygen supply to brain tissues caused by cerebral circulation disorder, cerebral metabolism disorder, or the like remarkably lowers the brain cell functions. The continuous decrease in oxygen supply to brain tissues is reported to inactivate physiological functions and to cause irreversible organic disorders [Folia Pharmacologica Japonica, 76, 655 (1980)]. Preventing the decreased oxygen supply to brain tissues can thus protect the failure of the brain functions.

Drugs improving cerebral circulation, cerebral vasodilators, cerebral metabolism accelerators, and the like are clinically used as medicines for treating cerebrovascular disorders. These medicines, however, exhibit only insufficient improvement in neurological symptoms or disorders of ability of dayly life in the patients, even though they are recognized to improve subjective symptoms. Therefore, development of a medicine possessing both cerebral metabolism improving effects and anti-amnesic activity based on prolyl endopeptidase inhibitory action has been desired.

The present inventors have undertaken extensive studies on various compounds in order to obtain an excellent medicine for improving cerebral circulation/metabolism and for preventing amnesia. As a result, the inventors have found that certain types of amino acid imide derivatives exhibit both prolyl endopeptidase inhibitory activity and cerebral circulation/metabolism improving activity at the same time, and hence can be an excellent medicine for improving cerebral circulation/metabolism and for treating or preventing amnesia. These findings have led to the completion of this invention.

SUMMARY OF THE INVENTION

Accordingly an object of this invention is to provide amino acid imide derivatives represented by formula (I):

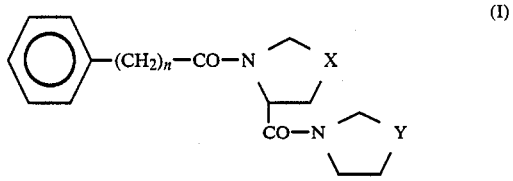

wherein n represents an integer of 0 to 5, and X and Y, which may be the same or different, represent a methylene group or a sulfur atom, provided that not both X and Y are methylene groups at the same time.

Another object of this invention is to provide a medicinal composition for treating or preventing cerebrovascular disorder, cerebral circulation disorder, cerebral metabolism disorder, or memory disturbance comprising an amino acid imide derivative of formula (I) as an essential component.

Still another object of this invention is to provide use of the amino acid imide derivative of formula (I) for preparing a medicinal composition for treating or preventing cerebrovascular disorder, cerebral circulation disorder, cerebral metabolism disorder, or memory disturbance.

Further object of this invention is to provide an intermediate compound for preparing the amino acid imide derivative of formula (I), which is N-substituted amino acid derivatives represented by formula (II,):

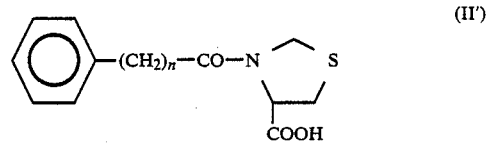

wherein n represents an integer of 1 to 5.

Other objects, features and advantages of the invention will hereinafter become more readily apparent from the following description.

DETAILED DESCRIPTION OF THE INVENTION AND PREFERRED EMBODIMENTS

Following compounds are given as typical amino acid imide derivatives of this invention:
N-(4-phenylbutanoyl)-L-thioprolylthiazolidineimide
N-(4-phenylbutanoyl)-D-thioprolylthiazolidineimide
N-(4-phenylbutanoyl)-L-thioprolylpyrrolidineimide
N-(4-phenylbutanoyl)-D-thioprolylpyrrolidineimide
N-(4-phenylbutanoyl)-L-prolylthiazolidineimide
N-(4-phenylbutanoyl)-D-prolylthiazolidineimide
N-(3-phenylpropionyl)-L-thioprolylthiazolidineimide
N-(3-phenylpropionyl)-D-thioprolylthiazolidineimide
N-(3-phenylpropionyl)-L-thioprolylpyrrolidineimide
N-(3-phenylpropionyl)-D-thioprolylpyrrolidineimide
N-(3-phenylpropionyl)-L-prolylthiazolidineimide
N-(3-phenylpropionyl)-D-prolylthiazolidineimide
N-(5-phenylpentanoyl)-L-thioprolylthiazolidineimide
N-(5-phenylpentanoyl)-D-thioprolylthiazolidineimide
N-(5-phenylpentanoyl)-L-prolylthiazolidineimide
N-(5-phenylpentanoyl)-D-prolylthiazolidineimide N-(6-phenylhexanoyl)-L-prolylthiazolidineimide
N-(6-phenylhexanoyl)-D-prolylthiazolidineimid
N-benzoyl-L-prolylthiazolidineimide
N-benzoyl-D-prolylthiazolidineimide The N-substituted amino acid imide derivatives of the present invention typified by the compounds enumerated above are prepared by the condensation reaction of an N-substituted amino acid of formula (II):

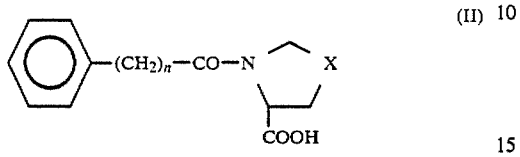
(II)

wherein n and X have the same meanings as previously defined and thiazolidine or pyrrolidine (where X is a sulfur atom).

Among N-substituted amino acid derivatives of formula (II) those in which n is 1 to 5 and X is a sulfur atom are novel compounds.

Following compounds are given as examples of this type of N-substituted amino acid derivatives:
N-(4-phenylbutanoyl)-L-thioproline
N-(4-phenylbutanoyl)-D-thioproline
N-(3-phenylpropionyl)-L-thioproline
N-(3-phenylpropionyl)-D-thioproline
N-(5-phenylpentanoyl)-L-thioproline
N-(5-phenylpentanoyl)-D-thioproline A conventional condensing agent can be used in the condensation reaction of an N-substituted amino acid derivative of formula (II) with thiazolidine or pyrrolidine. Preferable condensing agents are carbodiimides such as N-ethyl-N'-(3-dimethylaminopropyl)carbodiimide or its hydrochloride, N,N'-dicyclohexylcarbodiimide, or the like. Other conventional methods such as acid chloride method, mixed acid anhydride method, or activated ester method [Izumiya et al.; Peptide Synthesis -Fundamentals and Experiments; Maruzen Publishing Co. (1985)] may also be used for the condensation reaction of an N-substituted amino acid derivative of formula (II) with thiazolidine or pyrrolidine.

An N-substituted amino acid derivative of formula (II) is prepared by the reaction, in the presence or absence of a base, of a carboxylic acid halide of formula (III)

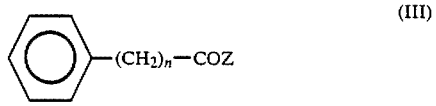
(III)

wherein n is an integer of 0 to 5 and Z represents a halogen atom; and an amino acid derivative of formula (IV):

(IV)

wherein X represents a methylene group or a sulfur atom.

A preferable base used for the reaction of compounds of formulae (III) and (IV) is an alkali metal hydroxide such as sodium hydroxide, potassium hydroxide, or the like. Other bases such as an alkali metal carbonate, a trialkyl amine, an aromatic amine, or the like can also be used. The reaction temperature is preferably room temperature or below. Any solvent which can dissolve the above-mentioned base may be used for the reaction.

Instead of the compound of formula (III) a compound represented by formula (III'):

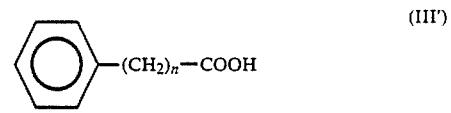
(III')

wherein n is an integer of 0 to 5, can be used for the reaction with a compound of formula (IV). In this reaction a carbodiimide compound is used as a condensing agent in the presence of a solvent which is inert to the reaction.

The compound of formula (I) of the present invention can be prepared in various dosing forms for oral or non-oral administration by formulating various pharmacologically acceptable carriers. When this compound is prepared in dosing forms for oral administration, it is appropriately formulated together with suitable additives, including excipients such as lactose, mannitol, corn starch, crystallized cellulose, etc., binders such as cellulose derivatives, gum arabic, gelatin, etc., disintegrators such as calcium carboxymethyl cellulose, etc., lubricants such as talc, magnesium stearate, etc., and the like. These may be formed into tablets, granules, powders, or capsules. These solid formulations can also be prepared in enteric coated pills using a coating substrate such as hydroxypropylmethyl cellulose phthalate, hydroxypropylmethyl cellulose acetate succinate, cellulose acetate phthalate, mathacrylate copolymer, or the like. Non-oral dosing forms include an injection, into which water, ethanol, glycerol, conventional surface active agents, and the like may be formulated. The compound of formula (I) can also be prepared in a suppository using a suitable suppository substrate.

Although the amount of dosage of the compound of formula (I) used may vary depending on the body weight, age, and symptoms of the subject, the intended treatment effect, the manner by which it is administered, and the period of administration, a generally appropriate amount may be from 1 to 2,000 mg per day, preferably from 10 to 200 mg per day, with the frequency of administration being 1 to 3 times per day.

Hereinafter are presented pharmacological experimental examples to further illustrate the effectiveness of the compound of formula (I). These examples are given for illustration of the invention and are not intended to be limiting thereof.

EXPERIMENTAL EXAMPLES

Experimental Example 1

<Inhibitory activity against prolyl endopeptidase from Flavobacterium>

Inhibitory activity of the compound of formula (I) against prolyl endopeptidase from Flavobacterium was measured according to the method of Yoshimoto and Tsuru [Arg. Biol. Chem., 42, 2419 (1978)] as outlined below.

Prolyl endopeptidase was dissolved with 20 mM Tris-HCl buffer (pH 7.4) at a concentration of 0.4 unit/ml. This solution (100 μl) was added to 890 μl of the same buffer, and the solution thus obtained was left at room temperature for 10 minutes. (This solution is herein referred to as an "Enzyme solution"). This buffer (990 μl) was used as a "Correction solution".

Test compound dissolved with dimethylsulfoxide (10 μl) was added to the Enzyme solution. The solution was stirred and allowed to stand at room temperature for 10 minutes. Separately, 10 μl of dimethylsulfoxide was added to Enzyme solution and was processed in the same manner. The solution thus obtained was served as a "Control solution". The same procedure was carried out on the Correction solution.

Two hundred microliters of 2.5 mM carbobezoxyglycylprolyl paranitroanilide, dissolved with 40% dioxane, was added to each of the above 3 solutions, i.e., the Enzyme solution with the test compound, Control solution, and Correction solution, and the reaction was carried out at 37° C. for 10 minutes.

After the addition of 2000 μl of a reaction termination solution [Triton X-100; 10 g/95 ml 1M acetate buffer (pH 4.0)], absorbances of the samples at 410 nm were measured using a spectrophotometer.

Enzyme activities were determined by subtracting the blank value, i.e., the absorbance measured on the Correction solution, from the absorbance of each of the sample solutions or of the Control solution.

Inhibition potency (IC$_{50}$) of the sample compound against prolyl endopeptidase was determined as the concentration of the compound (M) capable of inhibiting 50% of the enzyme activity of the control. The results are shown in Table 1.

TABLE 1

| Compounds | Inhibition Potency, IC$_{50}$ (M) |
| --- | --- |
| Compound of Ex. 1 | $8.7 \times 10^{-8}$ |
| Compound of Ex. 2 | $1.5 \times 10^{-7}$ |
| SUAM 1221* | $2.0 \times 10^{-7}$ |
| Aniracetam | $>10^{-3}$ |
| Calcium hopantenate | $>10^{-3}$ |

*The compound described in European Patent Publication No. 232849

Experimental Example 2

<Inhibitory activity against prolyl endopeptidase from brain>

Prolyl endopeptidase was prepared from canine brains according to the method of Yoshimoto et al [J. Biochem., 94, 325 (1983)].

Buffers used were:
Buffer A: 20 mM Tris-HCl buffer (pH 7.0)
Buffer B: a solution containing 0.1% gelatin, 1 mM EDTA, and 1 mM mercapto ethanol in buffer solution A Prolyl endopeptidase was dissolved with the Buffer B at a concentration of 0.4 unit/ml. This solution (50 μl) was added to 940 μl of the Buffer A, and the solution thus obtained was left at 37° C. for 10 minutes (This solution is herein referred to as "Enzyme solution"). A mixed solution of 50 μl of the Buffer B and 940 μl of Buffer A was used as a "Correction solution".

A test compound was dissolved with dimathylsulfoxide (10 μl) was added to the Enzyme solution. The mixture was stirred and allowed to stand at 37° C. for 10 minutes. Separately, 10 μl of dimethylsulfoxide was added to the Enzyme solution and was processed in the same manner. The solution thus obtained was served as a "Control solution". The same procedure was carried out on the Correction solution.

One hundred micoliters of 2.5 mM carbobezoxyglycylprolyl paranitroanilide, which was dissolved with 40% dioxane, was added to each of the above 3 solutions, i.e., the Enzyme solution with the test compound, Control solution, and Correction solution, and the reaction was carried out at 37° C. for 10 minutes.

After the addition of 100 μl of a reaction termination solution [50% acetic acid containing 10% Triton X-100], absorbances of the samples at 410 nm were measured using a spectrophotometer.

Enzyme activities were determined by subtracting the blank value, i.e., the absorbance measured on the Correction solution, from the absorbance of each of the sample solutions and of the Control solution.

Inhibition potency (IC$_{50}$) of the sample compound against prolyl endopeptidase was determined as the concentration of the compound (M) capable of inhibiting 50% of the enzyme activity of the control. The results are shown in Table 2.

TABLE 2

| Compounds | Inhibition Potency, IC$_{50}$ (M) |
| --- | --- |
| Compound of Ex. 1 | $1.7 \times 10^{-8}$ |
| Compound of Ex. 2 | $4.1 \times 10^{-8}$ |
| Compound of Ex. 3 | $3.1 \times 10^{-8}$ |
| SUAM 1221 | $7.6 \times 10^{-8}$ |

Experimental Example 3

<Anti-hypoxic activity>

Groups of ICR male mice, age 4 to 5 weeks, each group consisting of 10 mice and each mouse having been fasted for 24 hours, were used for the test. Mice were placed in a transparent desiccator (diameter: 19 cm, height: 30 cm) made of synthetic resin and having 2 bulbs, one at the upper portion and the other at the lower portion, for replacing the gas therein. A mixed gas (4% $O_2$ + 96% $N_2$) was fed from the upper bulb at a rate of 10 l/min to measure the period of time until respiratory arrest took place for each mouse. The time measured was taken as the time of survival.

Each tested compound suspended in 5% gum arabic solution was intraperitoneally administered 30 minutes before the start of the mixed gas feeding. A group of mice to which only 5% gum arabic solution was intraperitoneally administered was used as a control.

Compounds, not sufficiently suspended in 5% gum arabic, were dissolved with Tween 80 so that the final concentration of the detergent was 3%, followed by the addition of 5% gum arabic. The anti-hypoxic activity was determined according to the following formula:

$$\text{Anti-hypoxic Activity (\%)} = \frac{\text{Survival time of the group to which a test compound was administered}}{\text{Survival time of the control group}} \times 100$$

The results are shown in Table 3.

TABLE 3

| Compounds | Dose (mg/kg) | Anti-hypoxic Activity (%) |
| --- | --- | --- |
| Control | — | 100 |
| Compound of Ex. 1 | 100 | 124 |
| Compound of Ex. 2 | 100 | 160 |
| Compound of Ex. 3 | 100 | 169 |

TABLE 3-continued

| Compounds | Dose (mg/kg) | Anti-hypoxic Activity (%) |
|---|---|---|
| Compound of Ex. 4 | 100 | 164 |
| Aniracetam | 100 | 115 |
| Aniracetam | 300 | 159 |
| Calcium hopantenate | 250 | 135 |
| Idebenone | 100 | 140 |

Experimental Example 4

<Anti-amnesic activity>

Compounds of this invention were checked with respect to their abilities to prevent the inhibition of long-term memory fixation by cycloheximide which is an amnesia inducing compound. ICR male mice, age 6 to 7 weeks, were used for the test. The test was carried out using a step-down passive avoidance apparatus.

On the first day, a 5-minute training was given to each mouse which was placed on a rubber platform. Every time when the mouse stepped down on the grid floor, a 0.2 mA electric foot shock was applied until it stepped up on the platform. This motion of the mouse was repeated for 5 minutes.

Administration of cycloheximide and the compound of this invention was performed immediately after the training. Cycloheximide was dissolved in a saline and subcutaneously administered to the mouse. The compound of this invention, suspended in a sesame oil/-Tween 80/5% gum arabic (3/1/96; by volume), was intraperitoneally administered. Aniracetam suspended in 5% gum arabic was orally administered. Twenty-four hours after the training, a retention test was performed, which consisted of placing the mouse on the platform again and measuring the latency of the mouse to step down on the grid floor. The amnesia ratio for each group of mice was determined as the percentage of amnesic mice taken latency shorter than 150 seconds. The results are shown in Table 4.

TABLE 4

| Drug Treatment (Dose, Route of Administration) | | Number of Mice | Amnesic Mice (%) | Amnesia Reversal (%)* |
|---|---|---|---|---|
| vehicle (ip) + | saline (sc) | 16 | 12.5 | — |
| vehicle (ip) + | cycloheximide (200 mg/kg, sc) | 16 | 68.8 | — |
| Compd. of Ex. 1 (1 mg/kg, ip) + | cycloheximide (200 mg/kg, sc) | 17 | 52.9 | 28.2 |
| Compd. of Ex. 1 (3 mg/kg, ip) + | cycloheximide (200 mg/kg, sc) | 15 | 26.7 | 74.8 |
| vehicle (po) + | saline (sc) | 13 | 7.7 | — |
| vehicle (po) + | cycloheximide (200 mg/kg, sc) | 15 | 53.3 | — |
| aniracetam (30 mg/kg, po) + | cycloheximide (200 mg/kg, sc) | 14 | 42.9 | 22.8 |
| aniracetam (60 mg/kg, po) + | cycloheximide (200 mg/kg, sc) | 14 | 50.0 | 7.2 |

*Amnesia Reversal (%) = $\frac{\% Atc - \% Avc}{\% Avs - \% Avc}$ wherein %A is a percentage of amnesic mice, t denotes a test compound, c stands for cycloheximide, v stands for vehicle, and s stands for saline [Drugs Exptl. Clin. Res., IX (12), 853–871 (1983)].

Experimental Example 5

<Toxicity Experiment>

Intraperitoneal administration

Groups of ICR male mice, age 4 to 5 weeks, each group consisting of 10 mice were used for the test. A dose of 300 mg/kg of each compound prepared in Examples 1 and 2 hereinbelow suspended in 5% gum arabic was intraperitoneally administered to each group of mice. No fatal problem in mice was observed during a period of 7 days.

Oral administration

Groups of Fisher 344 male rats, age 6 weeks, each group consisting of 5 rats were used for the test. A dose of 500, 1,000, 1,500, and 2,000 mg/kg of each of the compounds prepared in Examples 1, 2 and 3, and SUAM 1221, each dissolved in propylene glycol was orally administered to each group of rats. No fatal problem nor the decrease in body weights in any groups of rats to which the compounds of this invention were administered, was observed during a period of 14 days. On the other hand, one rat died out of the 5 rats in the group to which 1,500 mg/kg of SUAM 1221 was administered, and 2 rats died out of the 5 rats in the group to which 2,000 mg/kg of SUAM 1221 was administered.

As fully described above, the compounds in this invention are superior to aniracetam, calcium hopantenate, idebenone, and SUAM 1221, the compound described in European Patent Publication No. 232849, in their prolyl endopeptidase inhibitory activities against prolyl endopeptidases from flavobacterium and canine brain, and anti-hypoxic activities. Their safety, i.e., non-toxicity, was also demonstrated to be excellent.

Other features of the invention will become apparent in the course of the following description of the exemplary embodiments which are given for illustration of the invention and are not intended to be limiting thereof.

EXAMPLES

EXAMPLE 1

N-(4-phenylbutanoyl)-L-thioprolylthiazolidineimide 6.65 g of L-thioproline was dissolved in 100 ml of 1N sodium hydroxide. After the addition of 50 ml of water to the solution, a solution prepared by dissolving 9.10 g of 4-phenylbutanoyl chloride in 50 ml of benzene was added dropwise with stirring. Subsequently, 50 ml of 1N sodium hydroxide was further added and the mixture was stirred overnight. The benzene layer was removed and the water layer was washed twice with 70 ml of ether. To this water layer was added 7% hydrochloric acid to acidify it, followed by extraction with 70 ml of ethyl acetate three times. The extract was dried over anhydrous sodium sulfate. Ethyl acetate was evaporated to obtain an oily residue, which was subjected to column chromatography on silica gel using chloroform-methanol as an eluent to obtain a fraction of 11.4 g of N-(4-phenylbutanoyl)-L-thioproline as colorless crystals.

mp: 93°–94° C.,

IT (KBr) cm$^{-1}$: 2400–3100, 1710, 1600, 1430, 1275, 1230, 1210.

NMR (CDCl$_3$) δ: 1.62–2.50 (4H, m), 2.62 (2H, t, J=6 Hz), 3.16 (2H, d, J=5 Hz), 4.37 (2H, s-like), 5.02 (1H, t, J=5 Hz), 7.1 (5H, s-like), 9.69 (1H, brs).

1.40 g of N-(4-phenylbutanoyl)-L-thioproline thus prepared was added to 20 ml of methylene chloride together with 445 mg of thiazolidine and 1.05 g of N-ethyl-N'-(3-dimethylaminopropyl) carbodiimide hydrochloride, and the mixture was stirred overnight. After the reaction, the mixture was washed with 1N hydrochloric acid, brine, saturated sodium bicarbonate, then brine, and was dried over anhydrous sodium sulfate. Methylene chloride was evaporated to obtain an oily residue, which was subjected to column chromatography on silica gel using chloroform-methanol as an eluent to obtain a fraction of 833 mg of N-(4-phenylbutanoyl)-L-thioprolylthiazolidineimide as colorless crystals.

mp: 80°–82° C.

$[\alpha]_D^{22}$ −93° (C=1, MeOH).

IR (KBr) cm$^{-1}$: 2940, 1635, 1420, 1410, 1340, 1265, 740, 700.

NMR (CDCl$_3$) δ: 1.64–2.6 (4H, m), 2.64 (2H, t, J=6 Hz), 2.79–4.26 (6H, m), 4.52 (4H, s-like), 5.03 (1H, t, J=7 Hz), 7.15 (5H, s-like).

EXAMPLE 2

N-(4-phenylbutanoyl)-L-prolylthiazolidineimide 11.5 g of N-(4-phenylbutanoyl)-L-proline in the form of colorless crystals was prepared in the same manner as described in Example 1 in connection with the preparation of N-(4-phenylbutanoyl)-L-thioproline, except 5.75 g of L-proline and 9.10 g of 4-phenylbutanoyl chloride were used.

3.92 g of N-(4-phenylbutanoyl)-L-proline thus prepared was added to 50 ml of methylene chloride together with 1.34 g of thiazolidine and 3.00 g of N,N'-dicyclohexylcarbodiimide, and the mixture was stirred overnight. After the reaction, the mixture was washed with 1N hydrochloric acid, brine, saturated sodium bicarbonate, then brine, and was dried over anhydrous sodium sulfate. Methylene chloride was evaporated to obtain an oily residue, which was subjected to column chromatography on silica gel using chloroform-methanol as an eluent to obtain a fraction of 2.37 g of N-(4-phenylbutanoyl)-L-prolylthiazolidineimide as a colorless oil.

IR (neat) cm$^{-1}$: 2950, 2880, 1650, 1425, 1320, 750, 700.

NMR (CDCl$_3$) δ: 1.44–2.38 (6H, m), 2.27 (2H, t, J=6 Hz). 2.65 (2H, t, J=6 Hz), 2.85–4.83 (7H, m), 4.53 (2H, s-like), 7.1 (5H, s-like).

Petroleum ether was added to this oily substance and the mixture was treated under ice-cooling to obtain the latter substance as crystals.

mp: 53°–55° C.

$[\alpha]_D^{22}$ −24° (C=1, MeOH).

IR (KBr) cm$^{-1}$: 2950, 1635, 1435, 1350, 1320, 1265, 740, 700.

NMR (CDCl$_3$) δ: 1.44–2.38 (6H, m), 2.27 (2H, t, J=6 Hz), 2.65 (2H, t, J=6 Hz), 2.85–4.83 (7H, m), 4.53 (2H, s-like), 7.16 (5H, s-like).

EXAMPLE 3

N-(4-phenylbutanoyl)-L-thioprolylpyrrolidineimide

From 8.40 g of N-(4-phenylbutanoyl)-L-thioproline prepared in Example 1 and 2.10 g of pyrrolidine, 5.50 g of N-(4-phenylbutanoyl)-L-thioprolylpyrrolidineimide in the form of colorless crystals was prepared in the same manner as described in the later part of Example 1 in connection with the preparation of N-(4-phenylbutanoyl)-L-thioprolylthiazolidineimide.

mp: 67°–70° C., $[\alpha]_D^{22}$ −105.6° (C=1, MeOH).

IR (KBr) cm$^{-1}$: 2880, 1635, 1445, 1410, 1290, 1160.

NMR (CDCl$_3$) δ: 1.53–2.37 (6H, m), 2.23 (2H, t, J=6 Hz), 2.67 (2H, t, J=6 Hz), 3.01–3.98 (6H, m), 4.55 (2H, s-like), 5.02 (1H, t, J=7 Hz), 7.14 (5H, s-like).

EXAMPLE 4

N-(4-phenylbutanoyl)-D-prolylthiazolidineimide 3.45 g of D-proline was dissolved in 60 ml of 1N of sodium hydroxide and 30 ml of water. To the solution thus obtained, a solution prepared by dissolving 5.56 g of 4-phenylbutanoyl chloride in 30 ml of benzene was added dropwise with stirring. Subsequently, 30 ml of 1N sodium hydroxide was further added and the mixture was stirred at room temperature overnight. The benzene layer was removed and the water layer was washed twice with 50 ml of ether. To this water layer was added 7% hydrochloric acid to acidify it, followed by extraction with 70 ml of ethyl acetate three times. The extract was dried over anhydrous sodium sulfate. Ethyl acetate was evaporated to obtain an oily residue, which was treated with hexane to obtain 5.28 g of N-(4-phenylbutanoyl)-D-proline as colorless crystals.

mp: 86°–87.5° C.

1.31 g of N-(4-phenylbutanoyl)-D-proline was added to 20 ml of methylene chloride together with 0.45 g of thiazolidine and 1.05 g of N-ethyl-N'-(3-dimethylaminopropyl) carbodiimide hydrochloride, and the mixture was stirred overnight at room temperature. After the reaction, the mixture was washed with 1N hydrochloric acid, brine, saturated sodium bicarbonate, then brine, and was dried over anhydrous sodium sulfate. Methylene chloride was evaporated to obtain an oily residue, which was subjected to column chromatography on silica gel using chloroform-methanol as an eluent to obtain a fraction of 662 mg of N-(4-phenylbutanoyl)-D-prolylthiazolidineimide as a colorless oil.

$[\alpha]_D^{22}$ +24° (C=1, MeOH).

| Preparation Example 1 | |
| --- | --- |
| Compound of Example 1 | 50 g |
| Lactose | 315 g |
| Corn starch | 125 g |
| Crystallized cellulose | 25 g |

The above components were blended to obtain a homogeneous mixture. After the addition of 200 ml of 7.5% hydroxypropyl cellulose, the mixture was made into granule by means of an extruding granulator using a screen with a 0.5 mm diameter. The granule was rounded and dried to produce a granulose preparation. The dried granule was coated with 1.9 kg of a film-coating liquid having the following composition using a fluid-type granulator to produce enteric coated granule.

| | |
|---|---|
| Hydroxypropylmethyl cellulose phthalate | 5.0 wt % |
| Stearic acid | 0.25 wt % |
| Methylene chloride | 50.0 wt % |
| Ethanol | 44.75 wt % |

Preparation Example 2

| | |
|---|---|
| Compound of Example 2 | 20 g |
| Lactose | 100 g |
| Corn starch | 36 g |
| Crystallized cellulose | 30 g |
| Calcium carboxymethyl cellulose | 10 g |
| Magnesium stearate | 4 g |

The above components were homogeneously mixed and prepared in tablets each weighing 200 mg by means of a one-shot tablet machine using a 7.5 mm screw.

Spray coating was applied to the tablets to prepare enteric film-coated tablets having the film weight of 10 mg per tablet. The composition of the coating liquid was as follows:

| | |
|---|---|
| Hydroxypropylmethyl cellulose phthalate | 8.0 wt % |
| Glycerol fatty acid ester | 0.4 wt % |
| Methylene chloride | 50.0 wt % |
| Breached beeswax | 0.1 wt % |
| Isopropanol | 41.5 wt % |

As illustrated above, the compounds of this invention exhibit both memory improving effects and cerebral circulation/metabolism improving effects because of their prolyl endopeptidase inhibitory activity, anti-hypoxic activity, and anti-amnesic activity. In addition, the compounds have a high degree of safety. Thus they are useful as medicines for treating or preventing cerebral hemorrhage sequela, cerebral infarction sequela, cerebral arterioscleosis, subarachnoid hemorrhage sequela, cranial injury sequela, cerebral operation sequela, cerebrovascular dementia, Parkinson's disease, Alzheimer's disease, Pick's disease, various anoxia toxicosis including, but not limited to anthracemia sequela, cerebral alcoholoism related diseases, and the like.

Obviously, numerous modifications and variations of the present invention are possible in light of the above teachings. It is therefore to be understood that the scope of the appended claims, the invention may be practiced otherwise than as specifically described herein.

What is claimed as new and desired to be secured by Letters Patent is:

1. N-substituted amino acid imide derivatives represented by formula (I):

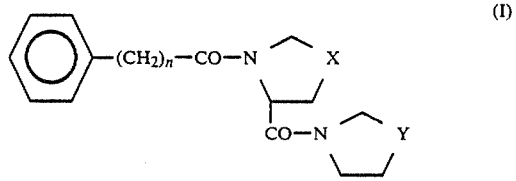

wherein n represents an integer of 0 to 5, and X and Y, which may be the same or different, represent a methylene group or a sulfur atom, provided that not both X and Y are methylene groups at the same time.

2. N-substituted amino acid imide derivatives according to claim 1, wherein said derivatives are specified L-configurations.

3. N-substituted amino acid imide derivatives according to claim 1, wherein said derivatives are specified D-configurations.

4. A medicinal composition comprising a compound defined in claims 1, 2, or 3 in an amount sufficient to inhibit prolyl endopeptidase and improve cerebral circulation/metabolism and physiologically acceptable carriers.

5. A method for treating or preventing cerebral circulation disorder, cerebral metabolism disorder, or memory disturbance, which comprises administering a compound defined in claims 1, 2, or 3 to the patient.

* * * * *